(12) United States Patent
Niendorf et al.

(10) Patent No.: US 10,513,748 B2
(45) Date of Patent: Dec. 24, 2019

(54) METHOD FOR MANUFACTURING A COMPONENT CONTAINING AN IRON ALLOY MATERIAL

(71) Applicant: SLM Solutions Group AG, Luebeck (DE)

(72) Inventors: Thomas Niendorf, Beverungen (DE); Hans Juergen Maier, Neustadt am Ruebenberge (DE); Florian Brenne, Paderborn (DE); Mirko Schaper, Salzkotten (DE); Guido Grundmeier, Wuerzburg (DE); Dieter Schwarze, Luebeck (DE)

(73) Assignee: SLM Solutions Group AG, Luebeck (DE)

( * ) Notice: Subject to any disclaimer, the term of this patent is extended or adjusted under 35 U.S.C. 154(b) by 815 days.

(21) Appl. No.: 14/877,532

(22) Filed: Oct. 7, 2015

(65) Prior Publication Data
US 2016/0201155 A1 Jul. 14, 2016

(30) Foreign Application Priority Data
Aug. 27, 2014 (EP) ..................... 14182482

(51) Int. Cl.
| | |
|---|---|
| *B22F 3/10* | (2006.01) |
| *C21D 9/00* | (2006.01) |
| *B33Y 10/00* | (2015.01) |
| *B33Y 70/00* | (2015.01) |
| *B33Y 80/00* | (2015.01) |
| *B23K 26/342* | (2014.01) |
| *B22F 3/00* | (2006.01) |
| *B22F 3/24* | (2006.01) |
| *B23K 26/00* | (2014.01) |
| *C21D 6/00* | (2006.01) |
| *C22C 38/00* | (2006.01) |
| *C22C 38/02* | (2006.01) |
| *C22C 38/04* | (2006.01) |
| *C22C 38/06* | (2006.01) |
| *C22C 38/20* | (2006.01) |
| *C22C 38/24* | (2006.01) |
| *C22C 38/26* | (2006.01) |

(Continued)

(52) U.S. Cl.
CPC .......... *C21D 9/0068* (2013.01); *A61L 27/042* (2013.01); *A61L 27/08* (2013.01); *A61L 27/58* (2013.01); *A61L 31/022* (2013.01); *A61L 31/024* (2013.01); *A61L 31/148* (2013.01); *B22F 3/008* (2013.01); *B22F 3/1055* (2013.01); *B22F 3/24* (2013.01); *B23K 26/0006* (2013.01); *B23K 26/342* (2015.10); *B33Y 10/00* (2014.12); *B33Y 70/00* (2014.12); *B33Y 80/00* (2014.12); *C21D 6/002* (2013.01); *C21D 6/005* (2013.01); *C21D 6/007* (2013.01); *C21D 6/008* (2013.01); *C22C 33/0207* (2013.01); *C22C 33/0257* (2013.01); *C22C 38/001* (2013.01); *C22C 38/002* (2013.01); *C22C 38/007* (2013.01); *C22C 38/02* (2013.01); *C22C 38/04* (2013.01); *C22C 38/06* (2013.01); *C22C 38/10* (2013.01); *C22C 38/12* (2013.01); *C22C 38/14* (2013.01); *C22C 38/16* (2013.01); *C22C 38/18* (2013.01); *C22C 38/20* (2013.01); *C22C 38/24* (2013.01); *C22C 38/26* (2013.01); *C22C 38/28* (2013.01); *C22C 38/30* (2013.01); *C22C 38/32* (2013.01); *C22C 38/34* (2013.01); *C22C 38/38* (2013.01); *B22F 2998/10* (2013.01); *B22F 2999/00* (2013.01); *B23K 2103/02* (2018.08); *Y02P 10/295* (2015.11)

(58) Field of Classification Search
CPC .................................................. C21D 9/0068
See application file for complete search history.

(56) References Cited

U.S. PATENT DOCUMENTS

| | | | |
|---|---|---|---|
| 2002/0193865 A1* | 12/2002 | Radisch | ................ A61L 31/022 |
| | | | 623/1.15 |
| 2010/0217370 A1 | 8/2010 | Scheuermann et al. | |
| 2014/0097277 A1 | 4/2014 | Kumta et al. | |

FOREIGN PATENT DOCUMENTS

| | | |
|---|---|---|
| DE | 102011121679 A1 | 6/2013 |
| EP | 2087915 A2 | 8/2009 |

(Continued)

OTHER PUBLICATIONS

Gibson, I., Rosen, D. W., and Stucker, B., Additive Manufacturing Technologies, 2010, Springer, New York (Year: 2010).*

(Continued)

*Primary Examiner* — Jophy S. Koshy
(74) *Attorney, Agent, or Firm* — Taft Stettinius & Hollister LLP

(57) ABSTRACT

In a method for manufacturing a component containing an iron alloy material, a pulverulent pre-alloy is provided. The pre-alloy comprises, in wt. %, 0.01 to 1% C, .01 to 30% Mn, ≤6% Al, and 0.05 to 6.0% Si, the remainder being Fe and usual contaminants. The pulverulent pre-alloy is mixed with at least one of elementary Ag powder, elementary Au powder, elementary Pd powder and elementary Pt powder so as to produce a powder mixture containing 0.1 to 20% of at least one of Ag, Au, Pd and Pt. The powder mixture is applied onto a carrier (16) by means of a powder application device (14). Electromagnetic or particle radiation is selectively irradiated onto the powder mixture applied onto the carrier (16) by means of an Irradiation device (18) so as to generate a component from the powder mixture by an additive layer construction method.

20 Claims, 2 Drawing Sheets

Figure 1:
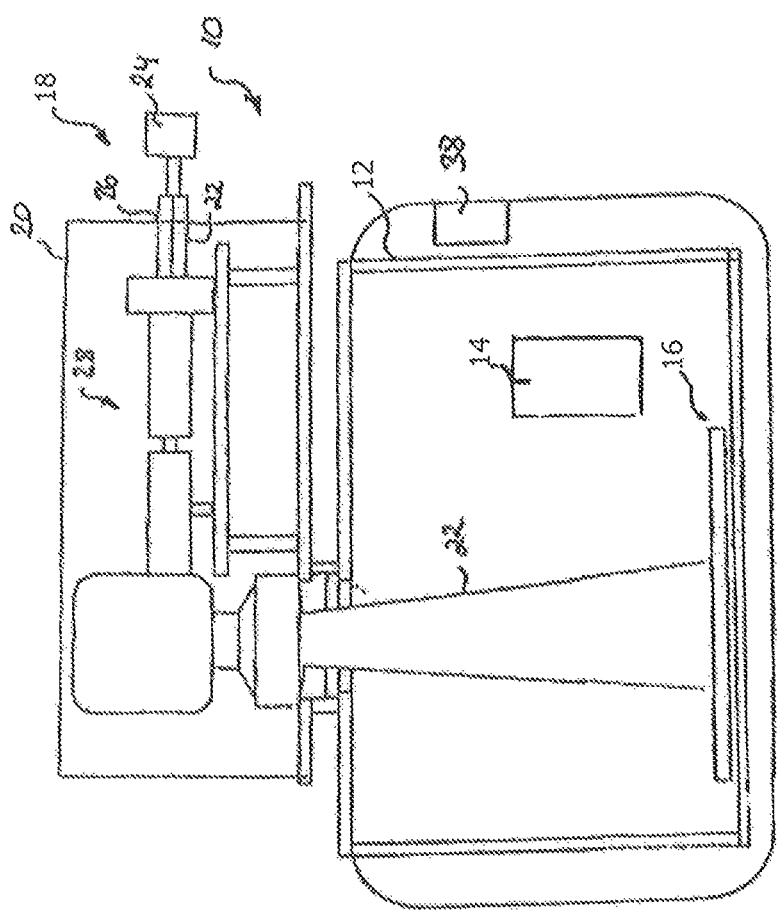

(51) Int. Cl.

| | |
|---|---|
| *C22C 38/28* | (2006.01) |
| *C22C 38/30* | (2006.01) |
| *C22C 38/32* | (2006.01) |
| *C22C 38/34* | (2006.01) |
| *C22C 38/38* | (2006.01) |
| *A61L 27/58* | (2006.01) |
| *B22F 3/105* | (2006.01) |
| *C22C 33/02* | (2006.01) |
| *A61L 27/04* | (2006.01) |
| *A61L 27/08* | (2006.01) |
| *A61L 31/02* | (2006.01) |
| *A61L 31/14* | (2006.01) |
| *C22C 38/10* | (2006.01) |
| *C22C 38/12* | (2006.01) |
| *C22C 38/14* | (2006.01) |
| *C22C 38/16* | (2006.01) |
| *C22C 38/18* | (2006.01) |
| *B23K 103/02* | (2006.01) |

(56) References Cited

FOREIGN PATENT DOCUMENTS

| EP | 1793979 B2 | 4/2014 |
|---|---|---|
| JP | H06184700 A | 7/1994 |
| JP | 2001254151 A | 9/2001 |
| JP | 2006249491 A | 9/2006 |
| RU | 2352679 C1 | 4/2009 |

OTHER PUBLICATIONS

ASM International Handbook Committee, ASM Handbook, vol. 04—Heat Treating—Heat Treating of Stainless Steels and Heat-Resistant Alloys, 1991, ASM International, p. 769-792. (Year: 1991).*

Notification of Reasons for Refusal, JP2015-167606, dated Aug. 30, 2018, with partial translation, 9 pages.

Notification of Reasons for Refusal, JP2015-167606, dated May 2, 2017, with partial translation, 8 pages.

European Patent Office, Examination Report issued in corresponding European application No. 14182482.1, dated Mar. 29, 2018, 8 pp.

Niendorf, et al., Steel showing twinning-induced plasticity processed by selective laser melting—An additively manufactured high performance material, Material Characterization 85, (2013), pp. 57-63.

European Search Report, EP14182482.1, SLM Solutions Group AG, dated Feb. 25, 2015, 9 pages.

* cited by examiner

METHOD FOR MANUFACTURING A COMPONENT CONTAINING AN IRON ALLOY MATERIAL

The present invention relates to a method for manufacturing a component containing an iron alloy material, an iron alloy material and a component, in particular an implant component, containing an iron alloy material.

Medical implants play an important role in modern surgical techniques. Implants which are intended to maintain in place in the body of a patient for a limited period of time only may be made of biodegradable or biocorrodible materials which, over time, are resorbed by the biological environment. An additional surgical treatment for removing the implant from the patient's body can thus be avoided. A biocorrodible iron alloy with the formula Fe—Mn—X is disclosed in EP 2 087 915 A2. In this iron alloy, the content of Mn is 5 to 30 wt. %. X is at least one element selected from the group of Pt, Pd, Ir, Rh, Re, Ru, and Os and is present in the alloy at a content of 0 to 20 wt. %.

Powder bed fusion is an additive layering process by which pulverulent, in particular metallic and/or ceramic raw materials can be processed to three-dimensional work pieces of complex shapes. To that end, a raw material powder layer is applied onto a carrier and subjected to laser radiation in a site selective manner in dependence on the desired geometry of the work piece that is to be produced. The laser radiation penetrating into the powder layer causes heating and consequently melting or sintering of the raw material powder particles. Further raw material powder layers are then applied successively to the layer on the carrier that has already been subjected to laser treatment, until the work piece has the desired shape and size. An apparatus for producing moulded bodies from pulverulent raw materials by a powder bed fusion process is described, for example, in EP 1 793 979 B1. Powder bed fusion may be used for the production of prototypes, tools, replacement parts, high value components or medical prostheses on the basis of CAD data.

An article by T. Niendorf and F. Brenne entitled "Steel showing twinning-induced plasticity processed by selective laser melting—An additively manufactured high performance material", Materials Characterization 85 (2013) 57-63 describes the processing of austenitic high-manganese steel showing twinning induced plasticity (TWIP) by powder bed fusion. In steels showing twinning induced plasticity, plastic deformation causes the formation of twin structures within the microstructure of the steel, resulting in excellent mechanical properties featuring high strength, good ductility and extraordinary strain hardening. Furthermore, austenitic high-manganese steels may also show transformation induced plasticity (TRIP), i.e. a plastic deformation of these steels may result in a microstructural transformation from austenite to martensite, leading to enhanced mechanical properties. TWIP steels processed by powder bed fusion exhibit mechanical properties which are similar to those of conventionally processed TWIP steels.

The invention is directed at the object of providing an effective and efficient method for manufacturing a component, in particular an implant component, containing a biocorrodible iron alloy material. Further, the invention is directed at the object of providing a cost-effective blocorrodible iron alloy material and a component, in particular an implant component, containing such an iron alloy material.

These objects are addressed by a method for manufacturing an iron alloy material as defined in claim 1, an iron alloy material as defined in claim 7 and a component as defined in claim 13.

In a method for manufacturing a component containing an iron alloy material, a pulverulent pre-alloy is provided. The pre-alloy powder may have any suitable particle size or particle size distribution. It is, however, preferable to process pre-alloy powders of particle sizes <100 µm. For example, a pre-alloy powder produced by spray aeration in argon inert atmosphere and having a mean particle diameter of approximately 40 µm may be used. The pulverulent pre-alloy comprises, in wt. %, 0.01 to 1% C, 0.0.01 to 30% Mn, ≤6% Al, and 0.05 to 6.0% Si, the remainder being Fe and usual contaminants such as, for example, P and/or S. In a preferred embodiment, the pulverulent pre-alloy comprises, in wt. %, 0.04 to 1% C, 9.0 to 24.0% Mn, 0.05 to 4% Al, and 0.05 to 6.0% Si, the remainder being Fe and usual contaminants. It is, however, also conceivable to use a pre-alloy which does not comprise any Al at all.

In the pre-alloy, the alloying element Mn, in particular when added at a content ≥9.0%, increases the corrosion rate in a biological environment and thus makes the pre-alloy more suitable for use as a biocorrodible material than pure iron. Furthermore, Mn acts as an austenite stabilizer, thus promoting the formation of face-centered cubic γ-iron in the microstructure of the pre-alloy. As compared to ferromagnetic α-iron, paramagnetic γ-iron does not interfere with the magnetic field of conventional magnetic resonance (MR) devices and hence should be the main phase in the microstructure of the pre-alloy in case the pre-alloy is intended to be used as an implant material. Furthermore, the alloying elements in the pre-alloy are selected and dosed such that the pre-alloy has a mixed crystal microstructure having a stacking fault energy which allows the pre-alloy to show at least one of twinning induced plasticity and transformation induced plasticity.

Addition of the alloying element C leads to a linear increase of the stacking fault energy. Furthermore, C influences the deformation mechanisms occurring beside the twin formation as well as the strength of the pre-alloy. In addition, C, like Mn, acts as an austenite stabilizer. Addition of the alloying element Al also leads to a linear increase of the stacking fault energy. Further, Al acts as a ferrit stabilizer, thus promoting the formation of body-centered cubic α-iron in the microstructure of the pre-alloy. Finally, Al counteracts hydrogen induced embrittlement and delayed cracking.

When Si is added to the pre-alloy, the stacking fault energy first is increased with an increasing Si-content, but, when further Si is added, is again decreased. Si, like Al, also acts as a ferrit stabilizer and increases both the strength and the wear resistance of the alloy. Finally, Si counteracts the formation of Fe-carbides and thus enhances the processing properties of semi-finished products by metallurgical methods.

The pulverulent pre-alloy is mixed with at least one of elementary Ag powder, elementary Au powder, elementary Pd powder and elementary Pt powder so as to produce a powder mixture containing 0.1 to 20% of at least one of Ag, Au, Pd and Pt. In a particularly preferred embodiment of the inventive method, elementary Ag powder is added to the pre-alloy powder at a content of 0.1 to 20%. Like the pre-alloy powder, the at least one of elementary Ag powder, elementary Au powder, elementary Pd powder and elementary Pt powder may have any suitable particle size or particle size distribution. It is, however, preferable to process powders of particle sizes <100 μm.

The powder mixture containing the pulverulent pre-alloy and the at least one of elementary Ag powder, elementary Au powder, elementary Pd powder and elementary Pt powder is applied onto a carrier by means of a powder application device. The carrier may be disposed in a process chamber and may be a rigidly fixed carrier having a surface onto which the powder mixture is applied. Preferably, however, the carrier is designed to be displaceable in vertical direction. The process chamber accommodating the carrier may be sealable against the ambient atmosphere, i.e. against the environment surrounding the process chamber, in order to be able to maintain a controlled atmosphere, in particular an inert atmosphere within the process chamber. Finally, electromagnetic or particle radiation is selectively irradiated onto the powder mixture applied onto the carrier by means of an irradiation device so as to generate a component from the powder mixture by an additive layer construction method. The irradiation device preferably is adapted to irradiate radiation onto the powder mixture which causes a site-selective melting of the powder particles. The irradiation device may comprise at least one radiation source, in particular a laser source, and at least one optical unit for guiding and/or processing a radiation beam emitted by the radiation source. The optical unit may comprise optical elements such an object lens, in particular an f-theta lens, and a scanner unit, the scanner unit preferably comprising a diffractive optical element and a deflection mirror.

By selectively irradiating a powder layer applied onto the carrier with electromagnetic or particle radiation, a first layer of the component is generated on the carrier. The additive layer construction method employed for generating the component may further include the steps of repeatedly vertically displacing the carrier so as to compensate for the height of the already generated layer(s) of the component, applying a further layer of powder onto the carrier such that the already generated layer(s) of the component is/are covered by the powder and selectively irradiating the layer of powder applied onto the already generated layer(s) of the component so as to generate a further layer of the component.

With the inventive method, a component can be generated from the powder mixture containing the pulverulent pre-alloy and the at least one of elementary Ag powder, elementary Au powder, elementary Pd powder and elementary Pt powder in a very efficient manner, even if the component has a complex shape. The control of the powder application device and the irradiation device is performed based on CAD data of the component to be generated. These CAD data can, for example, be derived from usual diagnostic data such as MR data, computed tomography (CT) data and the like. The method thus is in particular suitable for producing individually designed implant components.

The component generated by means of the method according to the invention may entirely consist of the iron alloy material generated when irradiating the above described powder mixture. It is, however, also conceivable that the component only in part is made of the iron alloy material and contains also other metallic or non-metallic materials. These materials may be processed either also in an additive layering process or may be joined to the part(s) made of the iron alloy material by any suitable joining method.

The component manufactured by the method according to the invention consists of an iron alloy material which, due to the composition of the pulverulent pre-alloy used for making the component, upon deformation shows at least one of twinning induced plasticity and transformation induced plasticity and hence exhibits excellent mechanical properties. Furthermore, by adding at least one of Ag, Au, Pd and Pt, the corrosion rate of the material in a biological environment can be significantly increased. Corrosion tests, which have been conducted for seven days in 0.9% NaCl aqueous solution at a pH of 6.5, revealed a mass loss of an iron pre-alloy containing (beside Fe and usual contaminants), in wt. %, 0.6 C, 22.4% Mn, 0.25% V, 0.2% Cr, and 0.25% Si of 1.7 mg per cm$^2$ sample surface per day as compared to 2.3 mg per cm$^2$ sample surface per day for the pre-alloy with an addition of 5 wt. % Ag.

The component thus is particularly suitable for use as a biocorrodible implant component.

While Au and Pt are effective in increasing the corrosion rate of the material in a biological environment, these alloying elements are rather expensive. However, the additive layer construction method according to the invention allows the component to be produced in a raw material saving manner so that even components containing expensive raw materials like Au and Pt can be manufactured at reasonable costs. Pd is cheaper than Au and Pt, but might not be entirely unproblematic regarding its toxicity when being released in a living body. Ag is less expensive than Au. However, due to its insolubility in liquid Fe, an Ag containing iron alloy material cannot be produced by conventional casting methods. Surprisingly, a material containing the above defined iron pre-alloy and Ag as an addition, however, can be manufactured by the additive layer construction method according to the invention. The inventive method thus can be employed to produce a biocorrodibie material which has not only excellent mechanical properties, but also desirable blocorrosion properties and which cannot be manufactured by conventional metallurgical methods.

In a preferred embodiment of the method for manufacturing a component containing an iron alloy material, the pulverulent pre-alloy further comprises at least one of Cr at a content of ≤2%, Cu at a content of ≤2%, Ti at a content of ≤2%, Co at a content of ≤2%, Zr at a content of ≤2%, V at a content of ≤2%, Nb at a content of ≤2%, Ta at a content of ≤2% and B at a content of ≤0.2%. In any case, the addition of the alloying elements has to be tailored in such a manner that the TWIP effect of the pre-alloy at room temperature is maintained. Furthermore, the biocompatibility of the alloying elements has to be considered, Ti, Zr, Nb and Ta being in particular suitable in this regard.

In the method for manufacturing a component containing an iron alloy material, the pulverulent pre-alloy may be mixed with at least one of elementary Ag powder, elementary Au powder, elementary Pd powder and elementary Pt powder so as to produce a powder mixture containing ≤20%, preferably ≤15%, in particular ≤10% and more particular ≤5% of at least one of Ag, Au, Pd and Pt. Additionally or alternatively thereto, the pulverulent pre-alloy may be mixed with at least one of elementary Ag powder, elementary Au powder, elementary Pd powder and elementary Pt powder so as to produce a powder mixture containing ≥0.5%, in particular ≥1% and more particular ≥2% of at least one of Ag, Au, Pd and Pt.

A suitable amount of at least one of elementary Ag powder, elementary Au powder, elementary Pd powder and elementary Pt powder to be mixed with the pre-alloy powder should be tailored in dependence on the desired properties of the iron alloy material component to be generated. At the one hand, the content of the addition Ag, Au, Pd and/or Pt should be high enough in order to provide for the desired high biocorrosion rate of the component to be generated. On the other hand, to much Ag, Au, Pd and/or Pt could affect the biocompatibility of the component if the amount of Ag, Au, Pd and/or Pt which is released upon degradation of the component within a living body exceeds a tolerance threshold. Furthermore, the amount of Ag, Au, Pd and/or Pt present in the microstructure of the generated iron alloy material should be low enough in order to ensure that the desired twinning induced plasticity and/or transformation induced plasticity behavior of the pre-alloy is not affected.

In a particular preferred embodiment of the method for manufacturing a component containing an iron alloy material, the operation of the powder application device and the irradiation device is controlled in such a manner that local melt pools are formed in the powder mixture upon being irradiated with electromagnetic or particle radiation. Within the melt pools both the pre-alloy and the at least one of elementary Ag, elementary Au, elementary Pd and elementary Pt are in the liquid state. The size of the melt pools depends on the size and the energy of the radiation beam irradiated onto the powder mixture and usually is larger than the diameter of the spot of the radiation beam. A typical spot diameter of the radiation beam irradiated onto the powder mixture is ≤100 μm. However, in any case, the size of the melt pools is very small as compared to the size of the component to be manufactured. As a result, the liquid metal in the melt pools solidifies at a high solidification rate. Preferably, the operation of the powder application device and the irradiation device is controlled in such a manner that the melt in the local melt pools solidifies at a solidification rate of up to approximately $7 \times 10^6$ K/s.

Due to having a higher density than the pre-alloy, the elementary addition does not "float" on the surface of the melt pool, but instead sinks—driven by gravity—in the direction of the bottom of the melt pools, i.e. in the direction of the already generated layers of the component to be produced. However, due to the high solidification rate of the liquid metal in the melt pools, the melt solidifies before accumulations of the elementary addition form at the bottom of the melt pools. Thus, upon solidification of the melt, the liquid elementary addition is more or less evenly distributed within the pre-alloy melt, even in case the elementary addition has a low solubility or, like Ag, is entirely insoluble in liquid Fe. Hence, in the resulting iron alloy material, a microstructure is obtained, wherein the elementary addition is finely dispersed and evenly distributed within a pre-alloy matrix.

The generated component may be heat-treated in order to modify its mechanical properties. For example, a heat treatment in an inert atmosphere, in particular in vacuum, for 1 hour at a temperature of 1050° C. is effective for increasing the average grain size of the material. As a result, the yield strength is reduced. However, the TWIP effect leads to a significant strengthening of the material and hence an increase of the failure strain. By suitably varying the time and the temperature of the heat treatment, the yield strength and the failure strain may be tailored. Further heat treatments may be performed in order to promote recovery and/or recrystallization. Thus, heat treatments for 1 minute to 24 hours at temperatures between 200° C. and 1100° C. may be performed as desired.

An iron alloy material according to the invention comprises, in wt. %, 0.01 to 1% C, 0.0001 to 30% Mn, ≤6% Al, 0.05 to 6.0% Si, and 0.1 to 20% Ag, the remainder being Fe and usual contaminants such as, for example, P and/or S. In a preferred embodiment, the iron alloy material comprises, in wt. %, 0.04 to 1% C, 9.0 to 24.0% Mn, 0.05 to 4% Al, and 0.05 to 6.0% Si, and 0.1 to 20% Ag, the remainder being Fe and usual contaminants. It is, however, also conceivable to use a pre-alloy which does not comprise any Al at all. Due to the insolubility of liquid Ag in an Fe melt, the iron alloy material according to the invention cannot be produced by conventional metallurgical methods. Surprisingly, it is, however, possible to manufacture the iron alloy material by using an additive layer construction method as described above.

The iron alloy material preferably further comprises at least one of Cr at a content of ≤2%, Cu at a content of ≤2%, Ti at a content of ≤2%, Co at a content of ≤2%, Zr at a content of ≤2%, V at a content of ≤2%, Nb at a content of ≤2%, Ta at a content of ≤2% and B at a content of ≤0.2%.

The Ag content of the iron alloy material preferably is ≤15%, in particular ≤10% and more particular ≤5%. Additionally or alternatively thereto, the Ag content of the iron alloy material may be ≥0.5%, in particular ≥1% and more particular ≥2%.

In the microstructure of the iron alloy material, Ag preferably is present in the form of Ag particles dispersed in an iron alloy matrix. The Ag particles may have particle sizes in the range of 30 to 50 μm. In general, in order to achieve a high corrosion rate, the Ag particles should be small in size and finely distributed within the iron alloy matrix. Additionally or alternatively thereto, in the microstructure of the iron alloy material, an iron alloy matrix is present which, upon plastic deformation of the iron alloy material, shows twinning induced plasticity and/or transformation induced plasticity. As a result, the iron alloy material exhibits excellent mechanical properties.

A component according to the invention contains an above described iron alloy material. The component may entirely consist of the iron alloy material. It is, however, also conceivable that the component only in part is made of the iron alloy material. The component in particular is an implant component which is intended to be implanted in a living body. Preferably the component is a biocorrodible component which corrodes and thus degrades over time when exposed to a biological environment.

Figure 2:
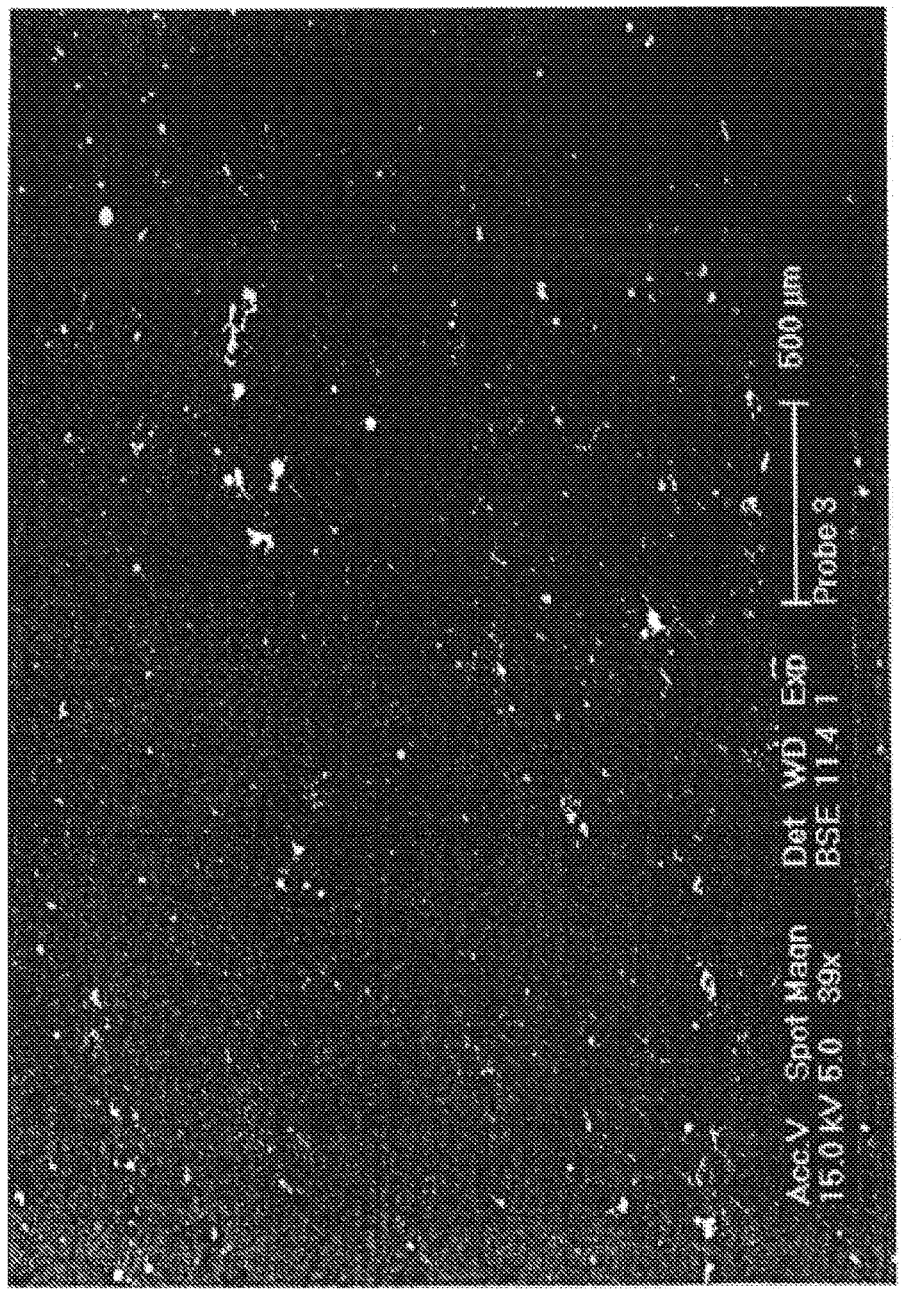

Preferred embodiments of the invention in the following are explained in greater detail with reference to the accompanying schematic drawings, in which:

FIG. 1 shows an apparatus for manufacturing a component containing an iron alloy material by an additive layer construction method, and FIG. 2 shows a SEM/BSE micrograph of the microstructure of an iron alloy material.

FIG. 1 shows an apparatus 10 for manufacturing a component by an additive layer construction method. The apparatus 10 comprises a process chamber 12. A powder application device 14, which is disposed in the process chamber 12, serves to apply a raw material powder onto a carrier 16. The process chamber 12 is sealable against the ambient atmosphere, i.e. against the environment surrounding the process chamber 12. The carrier 16 is designed to be displaceable in a vertical direction so that, with increasing construction height of a component, as it is built up in layers from the raw material powder on the carrier 16, the carrier 16 can be moved downwards in the vertical direction.

In case the apparatus 10 should be used for manufacturing a component containing an iron alloy material, the powder application device 14 is fed with a powder mixture obtained by mixing a pulverulent pre-alloy powder with at least one of elementary Ag powder, elementary Au powder, elementary Pd powder and elementary Pt powder so as to produce a powder mixture containing 0.1 to 20% of at least one of Ag, Au, Pd and Pt. If desired, a powder mixture may be produced which contains ≤15%, in particular ≤10% and more particular ≤5% of at least one of Ag, Au, Pd and Pt. Further, it is conceivable, to produce a powder mixture which contains ≥0.5%, in particular ≥1% and more particular ≥2% of at least one of Ag, Au, Pd and Pt.

The pre-alloy powder comprises, in wt. %, 0.01 to 1% C, 0.01 to 30% Mn, ≤6% Al, and 0.05 to 6.0% Si, the remainder being Fe and usual contaminants. If desired, the pre-alloy powder may further comprise at least one of Cr at a content of ≤2%, Cu at a content of ≤2%, Ti at a content of ≤2%, Co at a content of ≤2%, Zr at a content of ≤2%, V at a content of ≤2%, Nb at a content of ≤2%, Ta at a content of ≤2% and B at a content of ≤0.2%.

The apparatus 10 further comprises an irradiation device 18 for selectively irradiating laser radiation onto the raw material powder applied onto the carrier 16. By means of the irradiation device 18, the raw material powder applied onto the carrier 18 may be subjected to laser radiation in a site-selective manner in dependence on the desired geometry of the component that is to be produced. The irradiation device 18 has a hermetically sealable housing 20. A radiation beam 22, in particular a laser beam, provided by a radiation source 24, in particular a laser source which may, for example, comprise a diode pumped Ytterbium fibre laser emitting laser light at a wavelength of approximately 1070 to 1080 nm is directed into the housing 20 via an opening 26.

The irradiation device 18 further comprises an optical unit 28 for guiding and processing the radiation beam 22. The optical unit 28 may comprise a beam expander for expanding the radiation beam 22, a scanner and an object lens. Alternatively, the optical unit 28 may comprise a beam expander including a focusing optic and a scanner unit. By means of the scanner unit, the position of the focus of the radiation beam 22 both in the direction of the beam path and in a plane perpendicular to the beam path can be changed and adapted. The scanner unit may be designed in the form of a galvanometer scanner and the object lens may be an f-theta object lens. The operation of the irradiation device 18 and the operation of the powder application device 14 is controlled by means of a control unit 38.

During operation of the apparatus 10, a first layer of a component to be produced is generated on the carrier 16 by selectively irradiating the raw material powder layer applied onto the carrier 16 with the radiation beam 22. The radiation beam 22 is directed over the raw material powder layer applied onto the carrier 16 in accordance with CAD data of the component to be produced. After the first layer of the component to be produced is completed, the carrier 16 is lowered in a vertical direction allowing the application of a successive powder layer by means of the powder application device 14. Thereafter, the successive powder layer is irradiated by means of the irradiation device 18. Thus, layer by layer, the component is built up on the carrier 16.

In case the apparatus 10 is operated for manufacturing a component containing an iron alloy material, the operation of the powder application device 14 and the irradiation device 18, by means of the control unit 38, is controlled in such a manner that, due to the energy input from the radiation beam 22, local melt pools are formed in the powder mixture applied onto the carrier 16 upon being irradiated with the radiation beam 22. Within the melt pools, which are usually larger than the diameter of the spot of the radiation beam having a typical diameter of ≤100 μm, both the pre-alloy and the at least one of elementary Ag, elementary Au, elementary Pd and elementary Pt are in the liquid state, but solidify at a high a solidification rate up to approximately $7 \times 10^6$ K/s.

Due to having a higher density than the pre-alloy, the elementary addition does not "float" on the surface of the melt pool, but instead sinks—driven by gravity—in the direction of the bottom of the melt pools. However, due to the high solidification rate of the liquid metal in the melt pools, the melt solidifies before accumulations of the elementary addition form at the bottom of the melt pools. Thus, upon solidification of the melt, the liquid elementary addition is more or less evenly distributed within the pre-alloy melt, even in case the elementary addition has a low solubility or, like Ag, is entirely insoluble in liquid Fe. Hence, in the resulting iron alloy material, a microstructure is obtained, wherein the elementary addition is finely dispersed and evenly distributed within a pre-alloy matrix. In particular, in the microstructure of the iron alloy material, the elementary addition is present in the form of particles dispersed in an iron alloy matrix. The particles, for example, may have particle sizes in the range of 30 to 50 μm.

Due to the composition of the pre-alloy matrix, the iron alloy material, upon deformation, shows twinning induced plasticity and/or transformation induced plasticity. As a result, the iron alloy material exhibits excellent mechanical properties. Furthermore, due to the presence of at least one of Ag, Au, Pd and Pt in the microstructure of the iron alloy material, the iron alloy material shows high corrosion rates when exposed to a biological environment. The component therefore is particularly suitable for use as a biocorrodible implant component which is implanted in a living body, but corrodes and thus degrades over time when exposed to a biological environment.

EXAMPLE

For producing an iron alloy material by an additive layer construction method, a pulverulent pre-alloy powder having a mean particle diameter of 40 μm was produced by spray aeration in argon inert gas atmosphere. The composition of the pre-alloy powder was investigated by spark spectrometry and was determined to be, in wt. %, 0.6 C, 22.4% Mn, 0.25% V, 0.2% Cr, and 0.25% Si, the balance being Fe and usual impurities.

The pre-alloy powder was mixed with elementary Ag powder having particle diameters of 25 to 63 μm in a drum hoop mixer. The Ag powder was obtained by spray aeration in argon inert gas atmosphere. Powder mixtures containing 1 wt. %, 2 wt. % and 5 wt % Ag were obtained. The powder mixtures were processed in argon atmosphere using a SLM® 250$^{HL}$ machine (SLM Solutions GmbH) in combination with SLM® AutoFab software (Marcam Engineering GmbH) employing an yttrium fibre laser with a maximum power of 400 W. The microstructure of the iron alloy material generated from the powder mixture by an additive layer construction method was examined by SEM/BSE. Corrosion tests, were conducted for seven days in 0.9% NaCl aqueous solution at a pH of 6.5. The mechanical properties of the material were examined using samples having a size of 8×3×1.5 mm grinded with 5 μm abrasive paper. The servo-hydraulic testing machine was operated with a displacement rate of 20 μm/s.

The microstructure of an iron alloy material generated from the powder mixture containing 1 wt. % Ag by an additive layer construction method is depicted in FIG. 2. In the microstructure of the iron alloy material, Ag is present in the form of particles finely dispersed more or less in an iron alloy matrix. The particles have particle sizes in the range of 30 to 50 μm.

Furthermore, it was determined that the iron alloy material, due to the composition of the iron alloy matrix, upon deformation, shows transformation induced plasticity. The mechanical properties of the material at ambient temperature are summarized in Table 1 below.

TABLE 1

|  | $R_m$, MPa | $R_{p0.2}$, MPa |
|---|---|---|
| pre-alloy | 850 | 460 |
| pre-alloy + 1 wt. % Ag | 645 | 320 |
| pre-alloy + 2 wt. % Ag | 690 | 425 |
| pre-alloy + 5 wt. % Ag | 545 | 360 |

The presence of Ag in the microstructure of the iron alloy material leads to high corrosion rates. The corrosion test revealed a mass loss of the iron pre-alloy of 1.7 mg per cm² sample surface per day as compared to 2.3 mg per cm² sample surface per day for the pre-alloy with an addition of 5 wt. % Ag. The iron alloy material therefore is particularly suitable for making biocorrodible implant components.

The invention claimed is:

1. A method for manufacturing a component containing an iron alloy material, the method comprising the steps:
providing a pulverulent pre-alloy, the pre-alloy comprising in wt. %:
0.01 to 1% C,
0.01 to 30% Mn,
≤6% Al,
0.05 to 6.0% Si, and
at least one of Cr at a content of ≤2%, Cu at a content of ≤2%, Ti at a content of ≤2%, Co at a content of ≤2%, Zr at a content of ≤2%, V at a content of ≤2°/s, Nb at a content of ≤2%, Ta at a content of ≤2% and B at a content of ≤0.2%, the remainder being Fe and usual contaminants,
mixing the pulverulent pre-alloy with elementary Ag powder, so as to produce a powder mixture containing 0.5 to 20 wt. % Ag,
applying the powder mixture onto a carrier by a powder application device, and selectively irradiating electromagnetic or particle radiation onto the powder mixture applied onto the carrier by an irradiation device so as to generate a component from the powder mixture by an additive layer construction method.

2. The method according to claim 1, wherein the pulverulent pre-alloy is mixed with elementary Ag powder, so as to produce a powder mixture containing ≤5 wt. % Ag.

3. The method according to claim 1, wherein the pulverulent pre-alloy is mixed with elementary Ag powder, so as to produce a powder mixture containing ≥2 wt. % Ag.

4. The method according to claim 1, wherein an operation of the powder application device and the irradiation device is controlled in such a manner that local melt pools are formed in the powder mixture upon being irradiated with electromagnetic or particle radiation, and that the melt in the local melt pools solidifies at a solidification rate of approximately $7 \times 10^6$ K/s.

5. The method according to claim 1, wherein the generated component is heat-treated in an inert atmosphere for 1 minute to 24 hours at a temperature between 200° C. and 1100° C.

6. A method for manufacturing a component containing an iron alloy material, the method comprising the steps:
providing a pulverulent pre-alloy, the pre-alloy comprising in wt. %:
0.04 to 1% C,
9.0 to 24.0% Mn,
0.05 to 4% Al, and
0.05 to 6.0% Si, the remainder being Fe and usual contaminants,
mixing the pulverulent pre-alloy with at least one of elementary Ag powder, elementary Au powder, elementary Pd powder, and elementary Pt powder so as to produce a powder mixture containing 0.1 to 20 wt. % of at least one of Ag, Au, Pd and Pt,
applying the powder mixture onto a carrier by a powder application device, and
selectively irradiating electromagnetic or particle radiation onto the powder mixture applied onto the carrier by an irradiation device so as to generate a component from the powder mixture by an additive layer construction method.

7. The method of claim 6, wherein the pulverulent pre-alloy is mixed with at least one of elementary Ag powder, elementary Au powder, elementary Pd powder, and elementary Pt powder so as to produce a powder mixture containing ≤5 wt. % of at least one of Ag, Au, Pd and Pt.

8. The method of claim 7, wherein the pulverulent pre-alloy is mixed with elemental Ag powder so as to produce a powder mixture containing 0.1 wt. % to ≤5 wt. % Ag.

9. The method of claim 6, wherein the pulverulent pre-alloy is mixed with at least one of elementary Ag powder, elementary Au powder, elementary Pd powder and elementary Pt powder so as to produce a powder mixture containing ≥2 wt. % of at least one of Ag, Au, Pd and Pt.

10. The method of claim 9, wherein the pulverulent pre-alloy is mixed with elemental Ag powder so as to produce a powder mixture containing ≥2 wt. % to 20 wt. % Ag.

11. The method of claim 6, wherein an operation of the powder application device and the irradiation device is controlled in such a manner that local melt pools are formed in the powder mixture upon being irradiated with electromagnetic or particle radiation, and that the melt in the local melt pools solidifies at a solidification rate of approximately $7 \times 10^6$ K/s.

12. The method of claim 6, wherein the generated component is heat-treated in an inert atmosphere for 1 minute to 24 hours at a temperature between 200° C. and 1100° C.

13. The method of claim 6, wherein the pulverulent pre-alloy further comprises Cr at a content of ≤2 wt. %.

14. The method of claim 6, wherein the pulverulent pre-alloy further comprises, in wt. %, at least one of Cr at a content of ≤2%, Cu at a content of ≤2%, Ti at a content of ≤2%, Co at a content of ≤2%, Zr at a content of ≤2%, V at a content of ≤2%, Nb at a content of ≤2%, Ta at a content of ≤2% and B at a content of ≤0.2%.

15. A method for manufacturing a component containing an iron alloy material, the method comprising the steps:
providing a pulverulent pre-alloy, the pre-alloy comprising in wt. %:
0.01 to 1% C,
0.01 to 30% Mn,
≤6% Al, and
0.05 to 6.0% Si, the remainder being Fe and usual contaminants,
mixing the pulvenilent pre-alloy with elementary Ag powder so as to produce a powder mixture containing 0.1 to 20 wt. % Ag, applying the powder mixture onto a carrier by a powder application device, and selectively irradiating electromagnetic or particle radiation onto the powder mixture applied onto the carrier by an irradiation device so as to generate a component from the powder mixture by an additive layer construction method.

16. The method of claim 15, wherein the pulverulent pre-alloy is mixed with elemental Ag powder so as to produce a powder mixture containing 0.1 wt. % to ≤5 wt. % Ag.

17. The method of claim 15, wherein the pulverulent pre-alloy is mixed with elemental Ag powder so as to produce a powder mixture containing ≥2 wt. % to 20 wt. % Ag.

18. The method of claim 16, wherein the pulverulent pre-alloy further comprises, in wt. %, at least one of Cr at a content of ≤2%, Cu at a content of ≤2%, Ti at a content of ≤2%, Co at a content of ≤2%, Zr at a content of ≤2%, V at a content of ≤2%, Nb at a content of ≤2%, Ta at a content of ≤2% and B at a content of ≤0.2%.

19. The method of claim 17, wherein the pulverulent pre-alloy further comprises, in wt. %, at least one of Cr at a content of ≤2%, Cu at a content of ≤2%, Ti at a content of ≤2%, Co at a content of ≤2%, Zr at a content of ≤2%, V at a content of ≤2%, Nb at a content of ≤2%, Ta at a content of ≤2% and B at a content of ≤0.2%.

20. The method of claim 15, wherein an operation of the powder application device and the irradiation device is controlled in such a manner that local melt pools are formed in the powder mixture upon being irradiated with electromagnetic or particle radiation, and that the melt in the local melt pools solidifies at a solidification rate of approximately $7 \times 10^6$ K/s.

* * * * *